US006011003A

United States Patent [19]

Charnock-Jones et al.

[11] Patent Number: 6,011,003

[45] Date of Patent: Jan. 4, 2000

[54] FLT-4(FMS-LIKE TYROSINE KINASE), FLT-15, VARIANTS THEREOF USED AS GROWTH FACTOR INHIBITORS

[75] Inventors: David Stephen Charnock-Jones, Cambridge; Christine Ann Boocock, Dundee; Andrew Mark Sharkey; Stephen Kevin Smith, both of Cambridge, all of United Kingdom

[73] Assignee: Metris Therapeutics Limited, London, United Kingdom

[21] Appl. No.: 08/750,141

[22] PCT Filed: May 26, 1995

[86] PCT No.: PCT/GB95/01213

§ 371 Date: May 12, 1997

§ 102(e) Date: May 12, 1997

[87] PCT Pub. No.: WO95/33050

PCT Pub. Date: Dec. 7, 1995

[30] Foreign Application Priority Data

May 26, 1994 [GB] United Kingdom .................. 9410534

[51] Int. Cl.[7] .................................................. C07K 14/71

[52] U.S. Cl. ............................ 514/2; 536/23.5; 435/69.1; 530/350; 935/9; 935/11

[58] Field of Search .......................... 536/23.5; 435/69.1, 435/7.8, 361; 530/350; 514/2; 935/9

[56] References Cited

U.S. PATENT DOCUMENTS 5,861,484 1/1999 Kendall et al. ......................... 530/350

*Primary Examiner*—Lorraine Spector
*Attorney, Agent, or Firm*—Klauber & Jackson

[57] ABSTRACT

Disclosed is an altered, soluble form of the FLT polypeptide being capable of binding to VEGF and thereby exerting an inhibitory effect thereon, the polypeptide comprising five or fewer complete immunoglobulin-like domains, together with pharmaceutical compositions comprising the polypeptide, and various uses thereof.

6 Claims, 9 Drawing Sheets

FIG. 1(A)

```
     1                                                      50
kit  MRGARGAWDF LCVLLLLLRV QTGSSQPSVS PGEPSPPSIH PGKSDLIVRV
fms  .........M GPGVLLLLLV ATAWHGQGIP VIEPSVP... ....ELVVKP
flt  MVSYWDTGVL LCALLSCLLL TGSSSGSKLK DPELSLKG.. ...TQHIMQA

     51                                                    100
kit  GDEIRLLCTD PGFVKW.... ....TFEILD ETNENKQ... ....NEWITE
fms  GATVTLRCVG NGSVEWDGP. ....ASPHWT LYSDGSS... ....SILSTN
flt  GQTLHLQCRG EAAHKWSLPE MVSKESERLS ITKSACGRNG KQFCSTLTLN

     101                                                   150
kit  KAEATNTGKY TC....T... NKHGLSNSIY VFVRDPAKLF .....LVDRS
fms  NATFQNTGTY RC....TEPG DPLGGSAAIH LYVKDPARPW ....NVLAQE
flt  TAQANHTGFY SCKYLAVPTS KKKETESAIY IFISDTGRPF VEMYSEIPEI

     151                                                   200
kit  LYGKEDNDTL VRCPLTDPEV .TNYSLKGCQ GKPLPKD.LR FIPDPKAGIM
fms  VVVFEDQDAL LPCLLTDPVL EAGVSLVRVR GRPLMRH.TN YSFSPWHGFT
flt  IHMTEGRELV IPCRVTSPNI ..TVTLKKFP LDTLIPDGKR IIWDSRKGFI

     201                                                   250
kit  IKSVKRAYHR LCLHCSVDQE GKSVLSEKFI LKVRPAFKAV PVVSVSKASY
fms  IHRAK.FIQS QDYQCSALMG GRKVMSISIR LKVQKVIPGP PALTLVPAEL
flt  ISNAT.YKEI GLLTCEATVN GHLYKTNYLT HRQTNTIIDV QISTPRPVKL

     251                                                   300
kit  LLREGEEFTV TCTI.KDVSS SVYSTWKREN SQTKLQEK.. ..YNSWHHGD
fms  VRIRGEAAQI VCSA.SSVDV NFDVFLQHNN ..TKLAIP.. ..QQSDFHNN
flt  L..RGHTLVL NCTATTPLNT RVQMTWSYPD EKNKRASVRR RIDQSNSHAN

     301                                                   350
kit  FNYERQATLT ISSARVNDSG VFMCYANNTF GSANVTTTLE VVDKGFINI.
fms  .RYQKVLTLN LDQVDFQHAG NYSCVASNVQ GKHSTSMFFR VVESAYLNL.
flt  IFYS...VLT IDKMQNKDKG LYTCRVRSGP SFKSVNTSVH IYDKAFITVK

     351                                                   400
kit  FPMINTTVFV NDGENVDLIV EYEAFPKPEH QQWIYMNRTF TDKWEDYPKS
fms  SSEQNLIQEV TVGEGLNLKV MVEAYPGLQG .....FNWTY LGPFSDHQPE
flt  HRKQQVLETV AGKRSYRLSM KVKAFPSPEV V......... ......WLKD

     401                                                   450
kit  ENESN..... .IRYVSELHL TRLKGTEGGT YTFLVS..NS DVNAAIAFNV
fms  PKLANATTKD TYRHTFTLSL PRLKPSEAGR YSFLAR..NP GGWRALTFEL
flt  GLPATEKSAR YLTRGYSLII KDVTEEDAGN YTILLSIKQS NVFKNLTATL
```

FIG. 1(B)

```
     451                                                    500
kit  YVNTKPEI.. LTYDRL.... ...VN..GML QCVAAGFPEP TIDWYFCPGT
fms  TLRYPPEV.. SVIWTF.... ...INGSGTL LCAASGYPQP NVTWLQCSGH
flt  IVNVKPQIYE KAVSSFPDPA LYPLGSRQIL TCTAYGIPQP TIKWFWHPCN

     501                                                    550
kit  EQRC...... .......... .......... .......... ..........
fms  TDRCD..... .......... .......... .......... ..........
flt  HNHSEARCDF CSNNEESFIL DADSNMGNRI ESITQRMAII EGKNKMASTL

     551                                                    600
kit  .......... .......... .......... .......... ......SASV
fms  .......... .......... .......... .......... ......EAQV
flt  VVADSRISGI YICIASNKVG TVGRNISFYI TDVPNGFHVN LEKMPTEGED

     601                                                    650
kit  LPV..DVQTL NSSGPPF... .......... .......... ..GKLVVQSS
fms  LQVWDDPYPE VLSQEPF... .......... .......... ..HKVTVQSL
flt  LKLSCTVNKF LYRDVTWILL RTVNNRTMHY SISKQKMAIT KEHSITLNLT

     651                                                    700
kit  IDSSAFKHNG TVECKAYNDV G......... .......... ..........
fms  LTVETLEHNQ TYECRAHNSV G......... .......... ..........
flt  IMNVSLQDSG TYACRARNVY TGEEILQKKE ITIRDQEAPY LLRNLSDHTV

     701                                                    750
kit  ..KTSAYFNF A......... ..FKGNNKEQ IHPHTLFTP. ..........
fms  ..SGSWAF.I P......... ..ISAGAHTH PPDEFLFTP. ..........
flt  AISSSTTLDC HANGVPEPQI TWFKNNHKIQ QEPGIILGPG SSTLFIERVT

     751                                                    800
kit  .......... .......... .......... .......LLI GFVIVAGMMC
fms  .......... .......... .......... .......VVV ACMSIMALLL
flt  EEDEGVYHCK ATNQKGSVES SAYLTVQGTS DKSNLELITL TCTCVAATLF

     801                                                    850
kit  IIVMILTYKY LQKPMYEVQW KVVEEINGNN YVYID..PTQ LPYDH.KWEF
fms  LLLLLLLYKY KQKPKYQVRW KIIESYEGNS YTFID..PTQ LPYNE.KWEF
flt  WLLLTLLIRK MKRSSSEIKT DYLSIIMDPD EVPLDEQCER LPYDASKWEF

     851                                                    900
kit  PRNRLSFGKT LGAGAFGKVV EATAYGLIKS DAAMTVAVKM LKPSAHLTER
fms  PRNNLQFGKT LGAGAFGKVV EATAFGLGKE DAVLKVAVKM LKSTAHADEK
flt  ARERLKLGKS LGRGAFGKVV QASAFGIKKS PTCRTVAVKM LKEGATASEY
```

FIG. 1(C)

```
     901                                                   950
kit  EALMSELKVL SYLGNHMNIV NLLGACT.IG GPTLVITEYC CYGDLLNFLR
fms  EALMSELKIM SHLGQHENIV NLLGACT.HG GPVLVITEYC CYGDLLNFLR
flt  KALMTELKIL THIGHHLNVV NLLGACTKQG GPLMVIVEYC KYGNLSNYLK

     951                                                   1000
kit  RKRDSFI... ..C...SKQE DHAEAALYKN L......LHS KESSCSDSTN
fms  RKAEAML... ..GPSLSPGQ DPEGGVDYKN IHLEKKYVRR DSGFSSQGVD
flt  SKRDLFFLNK DAALHMEPKK EKMEPGLEQG KKPRLDSVTS SESFASSGFQ

     1001                                                  1050
kit  EYMDMKPGVS YVVPTKADKR RSVRIGSYIE RDVTPAIMED DELALDLEDL
fms  TYVEMRP... ..VSTSSN.. .....DSFSE QDLD....KE DGRPLELRDL
flt  EDKSL..... .......... .....SDVEE EEDSDGFYKE ...PITMEDL

     1051                                                  1100
kit  LSFSYQVAKG MAFLASKNCI HRDLAARNIL LTHGRITKIC DFGLARDIKN
fms  LHFSSQVAQG MAFLASKNCI HRDVAARNVL LTNGHVAKIG DFGLARDIMN
flt  ISYSFQVARG MEFLSSRKCI HRDLAARNIL LSENNVVKIC DFGLARDIYK

     1101                                                  1150
kit  DSNYVVKGNA RLPVKWMAPE SIFNCVYTFE SDVWSYGIFL WELFSLGSSP
fms  DSNYIVKGNA RLPVKWMAPE SIFDCVYTVQ SDVWSYGILL WEIFSLGLNP
flt  NPDYVRKGDT RLPLKWMAPE SIFDKIYSTK SDVWSYGVLL WEIFSLGGSP

     1151                                                  1200
kit  YPGMPVDSKF YKMIKEGFRM LSPEHAPAEM YDIMKTCWDA DPLKRPTFKQ
fms  YPGILVNSKF YKLVKDGYQM AQPAFAPKNI YSIMQACWAL EPTHRPTFQQ
flt  YPGVQMDEDF CSRLREGMRM RAPEYSTPEI YQIMLDCWHR DPKERPRFAE

     1201                                                  1250
kit  IV....QLIE KQISES.TNH I........Y SNLANCSPNR QKPVVDHSVR
fms  IC....SFLQ EQAQEDRRER D........Y TNLPSSSRS. .....GGSGS
flt  LVEKLGDLLQ ANVQQDGKDY IPINAILTGN SGFTYSTPAF SEDFFKESIS

     1251                                                  1300
kit  INSVGSTASS SQP......L LVHDDV.... .......... ..........
fms  SSSELEEESS SEH......L TCCEQGDIAQ PLLQPNNYQF C.........
flt  APKFNSGSSD DVRYVNAFKF MSLERIKTFE ELLPNATSMF DDYQGDSSTL

     1301                                                  1350
kit  .......... .......... .......... .......... ..........
fms  .......... .......... .......... .......... ..........
flt  LASPMLKRFT WTDSKPKASL KIDLRVTSKS KESGLSDVSR PSFCHSSCGH

     1351                                    1389
kit  .......... .......... .......... .........
fms  .......... .......... .......... .........
flt  VSEGKRRFTY DHAELERKIA CCSPPPDYNS VVLYSTPPI
```

FIG. 3(A)

| | | | | | |
|---|---|---|---|---|---|
| | 1410 | | | | |
| KDR | AGAGTGCGCC | AACGAGCCCA | GCCAAGCTGT | CTCAGTGACA | AACCCATACC |
| FLT | ACCCCTGTAA | CCATAACATT | CCGAAGCAAG | GTGTGACTTT | TGTTCCAATA |
| | 1460 | | | | |
| KDR | CTTGTGAAGA | ATGGAGAAGT | GTGGAGGACT | TCCAGGGAGG | AAATAAAATT |
| FLT | ATGAAGAGTC | CTTTATCCTG | GATGCTGACA | GCAACATGGG | AAACAGAATT |
| | 1510 | | | | |
| KDR | GAAGTTAATA | AAAATCAATT | TGCTCTAATT | GAAGGAAAAA | ACAAA----- |
| FLT | GAGAGCATCA | CTCAGCGCAT | GGCAATAATA | GAAGGAAAGA | ATAAG----- |
| FLT4 | GAGAGCATCA | CTCAGCGCAT | GGCAATAATA | GAAGGAAAGA | ATAAG----- |
| FLT15 | GAGAGCATCA | CTCAGCGCAT | GGCAATAATA | GAAGGAAAGA | ATAAGCTTCC |
| KDR | ---------- | ---------- | ---------- | ---------- | ---------- |
| FLT | ---------- | ---------- | ---------- | ---------- | ---------- |
| FLT4 | ---------- | ---------- | ---------- | ---------- | ---------- |
| FLT15 | ACCAGCTGAC | AGTTCTTTCA | TGTTGCCACC | TACAAGCTTC | TCTTCCAACT |
| | | | | 1555 | |
| KDR | ---------- | ---------- | ---------- | CTGTAAGTAC | CCTTGTTATC |
| FLT | ---------- | ---------- | ---------- | ATGGCTAGCA | CCTTGGTTGT |
| FLT4 | ---------- | ---------- | ---------- | ATGGCTAGCA | CCTTGGTTGT |
| FLT15 | ACTTCCATTT | CCTTCCG**TGA** | CTCTAAACGG | ATGGCTAGCA | CCTTGGTTGT |
| | 1575 | | | | |
| KDR | CAAGCGGCAA | ATGTGTCAGC | TTTGTACAAA | TGTGAAGCGG | TCAACAAAGT |
| FLT | GGCTGACTCT | AGAATTTCTG | GAATCTACAT | TTGCATAGCT | TCCAATAAAG |
| FLT4 | GGCTGACTCT | AGAATTTCTG | GAATCTACAT | TTGCATAGCT | TCCAATAAAG |
| FLT15 | GGCTGACTCT | AGAATTTCTG | GAATCTACAT | TTGCATAGCT | TCCAATAAAG |
| | 1625 | | | | |
| KDR | CGGGAGAGGA | GAGAGGGTGA | TCTCCTTCCA | CGTGACCAGG | ---------- |
| FLT | TTGGGACTGT | GGGAAGAAAC | ATAAGCTTTT | ATATCACAGA | ---------- |
| FLT4 | TTGGGACTGT | GGGAAGAAAC | ATAAGCTTTT | ATATCACAGA | ATTGTCAAAC |
| FLT15 | TTGGGACTGT | GGGAAGAAAC | ATAAGCTTTT | ATATCACAGA | ---------- |
| KDR | ---------- | ---------- | ---------- | ---------- | ---------- |
| FLT | ---------- | ---------- | ---------- | ---------- | ---------- |
| FLT4 | TTTGAGTGCC | TTCATCCTTG | CTCTCAGGAA | **TAG**AACTCTA | CCTCATCGGA |
| FLT15 | ---------- | ---------- | ---------- | ---------- | ---------- |

FIG. 3(B)

```
          1665
KDR    -----GGTCC T---GAAATT ACTTTGCAAC CTGACATGCA GCCCACTGAG
FLT    -----TGTGC CAAATGGGTT TCATGTTAAC TTGGAAAAAA TGCCGACGGA
FLT4   TCTCATGTGC CAAATGGGTT TCATGTTAAC TTGGAAAAAA TGCCGACGGA
FLT15  -----TGTGC CAAATGGGTT TCATGTTAAC TTGGAAAAAA TGCCGACGGA

       1710
KDR    CAGGAGAGCG TGTCTTTGTG GTGCACTGCA GACAGATCTA CGTTTGAGAA
FLT    AGGAGAGGAC CTGAAACTGT CTTGCACAGT TAACAAGTTC TTATACAGAG

FLT4   AGGAGAGGAC CTGAAACTGT CTTGCACAGT TAACAAGTTC TTATACAGAG
FLT15  AGGAGAGGAC CTGAAACTGT CTTGCACAGT TAACAAGTTC TTATACAGAG

       1760
KDR    CCTCACATGG TACAAGCTTG GCCCACAGCC TCTGCCAATC CATGTGGGAG
FLT    ACGTTACTTG GATTTTACTG CGGACAGTTA ATAACAGAAC AATGCACTAC
FLT4   ACGTTACTTG GATTTTACTG CGG
FLT15  ACGTTACTTG GATTTTACTG CGG

       1810
FLT    AGTATTAGCA AGCAAAAAAT GGCCATCACT AAGGAGCACT CCATCACTCT

       1860
FLT    TAATCTTACC ATCATGAATG TTTCCCTGCA AGATTCAGGC ACCTATGCCT

       1910
FLT    GCAGAGCCAG GAATGTATAC ACAGGGGAAG AAATCCTCCA GAAGAAAGAA
```

FIG. 5

FLT4

1 ESITQRMAII EGKNKMASTL VVADSRISGI YICIASNKVG TVGRNISFYI

51 TELSNFECLH PCSQE*

FLT15

1 ESITQRMAII EGKNKLPPAD SSFMLPPTSF SSNYFHFLP*

FLT-4(FMS-LIKE TYROSINE KINASE), FLT-15, VARIANTS THEREOF USED AS GROWTH FACTOR INHIBITORS

This application is the national stage of PCT/GB95/01213, filed May 26, 1995.

FIELD OF THE INVENTION

This invention relates to substances which inhibit growth factors, in particular, vascular endothelial growth factor (VEGF), methods of inhibiting growth factors and of treating tumours and regulating fertility.

BACKGROUND OF THE INVENTION

A considerable number of human growth factors are now known, many of which have been at least partly characterised. Among them is vascular endothelial growth factor (VEGF), which has been identified in several tissues (Gospodarowicz et al., 1989 PNAS 86, 7311–7315; Conn et al., 1990 PNAS 87, 2628–2632; Tischer et al., 1991 J. Biol. Chem. 266, 11947–11954). As its name suggests, this growth factor is a highly specific mitogen for endothelial cells and is greatly involved in angiogenesis. VEGF is a homodimeric glycoprotein of two 23 kDa subunits exhibiting sequence homology with platelet-derived growth factor A and B chains and placenta growth factor.

The homologous tyrosine kinase receptors fms-like tyrosine kinase receptor (FLT) and kinase insert domain-containing receptor (KDR) function as high-affinity VEGF receptors (de Vries et al., 1992 Science 255, 989–991; Terman et al., 1992 Biochem. Biophys. Res. Commun. 187, 1579–1586). Both FLT and KDR are membrane-spanning receptors that each contain seven immunoglobulin-like domains in the extracellular ligand-binding region, an intracellular tyrosine kinase domain and a transmembrane domain. The transmembrane domain serves to anchor the receptor in the cell membrane of the cells in which it is expressed.

A number of membrane-bound receptor molecules have been found to exist in truncated soluble forms, generated either by proteolytic processing or by alternative splicing of mRNA. Recently, Kendall & Thomas (1993 PNAS 90, 10,705–10,709, and WO94/21679) described the discovery of a soluble form of FLT receptor (sFLT) generated by alternative splicing.

Essentially, Kendall & Thomas screened a human umbilical vein endothelial cell (HUVEC) cDNA library with one probe specific for the 3' end of the fit coding region (encoding the intracellular tyrosine kinase domain) and with another probe specific for the 5' fit coding portion (encoding one of the extracellular N terminal domains). Clones which hybridised with the 5' specific probe but not with the 3' specific probe were selected for further study. In this way, a clone was isolated which encoded a soluble FLT polypeptide lacking the transmembrane domain and the intracellular domain. The truncation resulted from "readthrough" to an intronic termination codon. It was suggested by Kendall & Thomas that the soluble receptor could act as an efficient specific antagonist of VEGF in vivo.

The present invention is based on the discovery of further soluble variants of FLT, the existence of which was not predicted by the teaching of Kendall & Thomas.

SUMMARY OF THE INVENTION

In a first aspect the invention provides an altered, soluble form of the FLT polypeptide being capable of binding to VEGF and therebv exerting an inhibitory effect thereon, the polypeptide comprising five or fewer complete immunoglobulin-like domains. Preferably, the altered FLT polypeptide comprises four or fewer complete Ig-like domains. The altered soluble FLT polypeptide inhibits VEGF by preventing it binding to its natural receptors, fit and KDR, present on the surface of target cells. Surprisingly, such truncated forms, lacking a major extracellular portion of the molecule, are believed to retain affinity for VEGF.

The term "soluble" as used herein is intended to refer to altered forms of the FLT polypeptide which do not comprise a transmembrane domain and thus generally do not become associated with the cell membrane of cells in which the molecule is expressed. In particular, the invention provides soluble altered forms of the FLT polypeptide consisting substantially of four or five complete immunoglobulin-like domains.

In a particular embodiment the invention provides an altered, soluble form of FLT having at its C-terminus a region substantially having the amino acid sequence of the sequences termed FLT4 or FLT15 shown in FIG. 5, or a functional equivalent thereof. The term "functional equivalent" as used above is intended to include those polypeptides which have substantially the same deletions as the polypeptides encoded by FLT4 (SEQ ID NO:8) or FLT15 (SEQ ID NO:9) (with respect to the unaltered full length FLT molecule), but which may also have other deletions, additions or substitutions, (in particular conservative substitutions), and which retain an inhibitory effect for VEGF.

Preferably the polypeptide will also comprise, at its N-terminus, the amino acid sequence substantially corresponding to the equivalent portion of the unaltered wild-type FLT polypeptide. Conveniently, polypeptides in accordance with the invention will comprise around 400 to 500 amino acid residues, preferably around 480 amino acid residues, most preferably between 480 and 440 amino acid residues of the wild type FLT sequence. Preferably the polypeptides of the invention arise by alternative splicing of mRNA or by proteolytic processing of a mature polypeptide, although it will be apparent to those skilled in the art that the polypeptide could be encoded by a nucleic acid derived, at least in part, by recombinant DNA technology.

In a further aspect the invention provides a nucleic acid sequence encoding a polypeptide in accordance with the invention. In a particular embodiment the invention provides a nucleic acid comprising the sequence of nucleotides inserted at position 1655 of the FLT 4 sequence shown in FIG. 3 or the sequence of nucleotides inserted at position 1555 of the FLT 15 sequence shown in FIG. 3, or a functional equivalent thereof. Examples of functionally equivalent nucleic acids include those sequences which encode substantially the same polypeptide as those encoded by FLT4 or FLT15 but which differ in nucleotide sequence as a result of the degeneracy of the genetic code. It will be apparent to those skilled in the art that the portion of the inserted nucleotide sequence in FLT4 and FLT15 occurring after the premature termination codon could be omitted without affecting the characteristics of the encoded polypeptide. Accordingly, nucleic acid molecules without such sequences are also regarded as functionally equivalent for the purposes of the present invention.

Conveniently, the nucleic acid will substantially comprise the nucleotide sequence of FLT4 or FLT15 shown in FIG. 3, together with the nucleotide sequence encoding the N-terminus of unaltered, wild-type FLT. Advantageously, the nucleic acid will be obtainable by means of PCR amplification from a sample of human cells. Desirably, the nucleic acid will be obtainable by means of PCR using primers intended to hybridise to non-conserved regions of the FLT molecule. Conveniently, the nucleic acid sequence will be obtainable by use of PCR primers designed to hybridise to the regions of the FLT sequence shown underlined in FIG. 3. or immediately adjacent thereto. In particular, the PCR primers will conveniently have substantially the sequence: 5'-GCAAGGTGTGACTTTGTTC-3' (SEQ ID NO:10) and 5'-AGGATTTCTTCCCCTGTGTA-3' (SEQ ID NO:11).

In another aspect, the invention provides a method of inhibiting VEGF in vitro, comprising adding an effective amount of the polypeptide defined above. It may also be desirable to inhibit VEGF in a human subject. Thus the invention provides a method of inhibitng VEGF in a human subject, comprising administering an effective amount of the polypeptide defined above, together with a physiologically acceptable carrier substance. In particular, VEGF provides a mitogenic stimulus (particularly involved in angiogenesis), so inhibition of VEGF would be expected to provide therapeutic effects in the treatment of tumours or disorders involving inappropriate neovascularisation.

In particular the invention provides for a method of treating tumours or diseases involving inappropriate neovascularisation, comprising administering an effective amount of the polypeptide defined above, together with a physiologically acceptable carrier substance. Suitable diseases which might be amenable to treatment include ovarian cancer and ovarian hyperstimulation (Boocock et al., 1995 J. Natl. Cancer Inst. 87, 506–516).

Furthermore, it has been conclusively demonstrated that FLT is expressed by trophoblasts and cells from ovarian and endometrial tissues (Charnock-Jones et al., 1994 Biology of Reproduction 51, 524–530), which clearly suggests a role for VEGF in the growth and differentiation of trophoblasts during implantation.

Thus, in particular, the invention provides a method of affecting the growth and/or migration of trophoblasts, ovarian or endometrial cells by inhibiting the action of VEGF, comprising administering an effective amount of the polypeptide defined above, together with a physiologically acceptable carrier substance.

It will be appreciated by those skilled in the art that the identification of FLT on the surface of trophoblasts and endometrial cells also provides a number of possible methods of regulating fertility. For example, the growth of trophoblasts is essential for successful implantation of the embryo. Inhibition of trophoblast growth thus provides a method of contraception or contragestion.

Thus in a further aspect the invention provides a method of regulating the fertility of a human female, comprising administering an effective amount of the polypeptide defined above, together with a physiologically acceptable carrier substance. An "effective amount" of the polypeptide is an amount sufficient to substantially block the stimulus of VEGF on trophoblasts and/or endometrial cells. Typically, the method will result in reducing the fertility of the female.

Moreover, it might be possible to identify agents which can enhance the effect of VEGF on trophoblasts, and thereby improve the probability of successful implantation, either in assisted or spontaneous cycles. Candidates for such VEGF-enhancing agents would include anti-sense equivalents of the nucleic acid sequences encoding the truncated FLT polypeptides of the invention. It will be apparent to those skilled in the art that these could be used to improve the fertility of a human female.

In a further aspect the invention provides a pharmaceutical composition comprising the polypeptide defined above, together with a physiologically acceptable carrier substance. The composition could be used in vivo any one of the methods defined above. In yet another aspect the invention provides for the use of a polypeptide in accordance with the invention in the preparation of a therapeutic composition for the treatment of tumours and diseases involving inappropriate neovascularisation. Examples of such conditions and diseases are detailed, inter alia, in WO94/10202 and WO94/21679. The invention also includes within its scope a method of making a pharmaceutical compostion, comprising mixing the polypeptide defined above together with a physiologically acceptable carrier substance.

The invention will now be described by way of the following illustrative examples and with reference to the drawings.

DESCRIPTION OF THE DRAWINGS

FIG. 5 shows the C terminal amino acid sequences of two polypeptides (FLT4, SEQ ID NO:8, and FLT15, SEQ ID NO:9 respectively) in accordance with the invention.

EXAMPLE

Expression of FLT, the VEGF receptor, was investigated in cell lines derived from human trophoblast-like and ovarian and endometrial carcinomas. The trophoblast-like (choriocarcinoma) cell line used was BeWo (obtained from the American Type Culture Collection, Rockville Md., USA). The endometrial carcinoma cell lines were Ishikawa (obtained from Professor M Nishide, University of Tsukuba, Japan), and HEC 1-A and HEC 1-B (from ATCC, USA). The ovarian cancer cell lines were 7, 17R, 25, 25R and 35. These were all shown to be of epithelial origin and had been established in culture for 10–30 passages. Cell lines 17R and 25R were derived after chemotherapy and subsequent relapse (line 25R originating from the same patient as line 25).

BeWo cells were grown in Ham's F12, according to ATCC recommendations. Endometrial carcinoma lines were grown in McCoy's medium (ICN Flow Laboratories, Irvine, UK) with 10% foetal calf serum (ICN Flow) plus 2 mM L-glutamine (ICN Flow) and 50 U/ml and 50 mg/ml penicillin/streptomycin (ICN Flow).

It was decided to investigate expression of FLT in these cell lines and normal tissues by performing PCT and in situ hybridization. It was therefore necessary to construct suitable oligonucleotide primers and probes.

Figure 1:
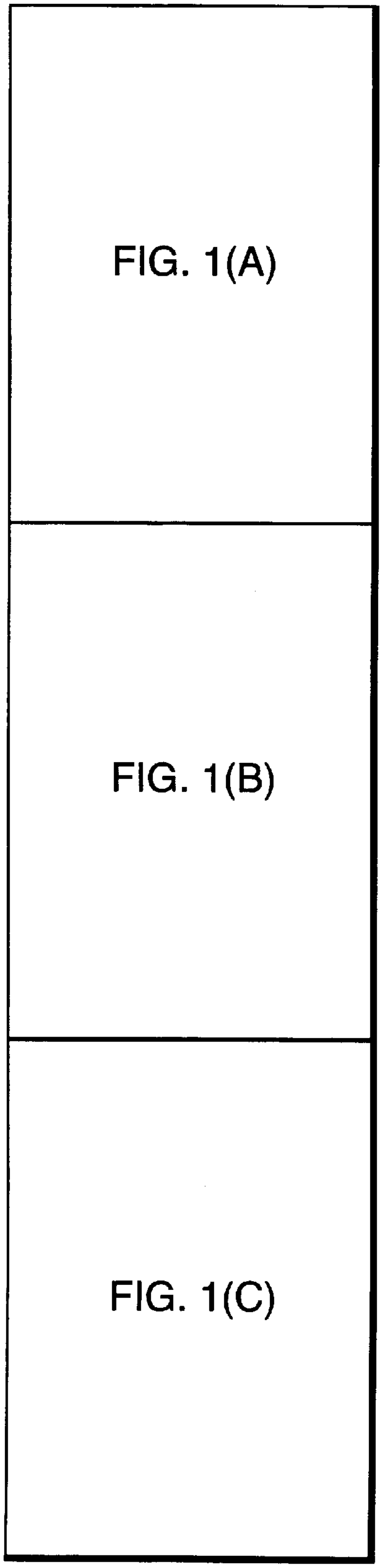
FIG. 1 shows an amino acid multiple alignment of closely related tyrosine kinase receptors (flt (SEQ ID NO:3), fms (SEQ ID NO:2) and kit (SEQ ID NO:1), "kit" being another name for KDR)

To help design appropriate primers, a protein multiple alignment of closely related tyrosine kinase receptors (FLT, FMS and KIT) was constructed (shown in FIG. 1) using the computer program "pileup". This revealed regions of divergent sequence among this family of receptors. The regions chosen for primer design are shown with double underlining in FIG. 1. The following nested PCR primers were then synthesized based on these protein sequences:

A) 5' GCAAGGTGTGACTTTTGTTC 3' (SEQ ID NO:10)

B) 5' GCGCTCGAGAGCATCACTCAG 3' (SEQ ID NO:13)

C) 5' GCGCGGCCGCAGTAAAATCCA 3' (SEQ ID NO:14)

D) 5' AGGATTTCTTCCCCTGTGTA 3' (SEQ ID NO:11)

The underlined portions of these oligonucleotides are the regions which hybridise to the flt cDNA sequence. The other nucleotides were added to facilitate directional cloning. The cycles used were: first round with primers A and D [95° C. 30 seconds, 55° C. 30 seconds, 72° C. 30 seconds]×25; second round with primers B and C: [95° C. 30 seconds, 44° C. 30 seconds, 72° C. 30 seconds]×2 [95° C. 30 seconds, 65° C. 30 seconds, 72° C. 30 seconds]×25. The internal primers B and C had sites for the restriction enzymes Xho I and Eag I respectively at their 5' ends to permit directional cloning of the products.

Figure 2:
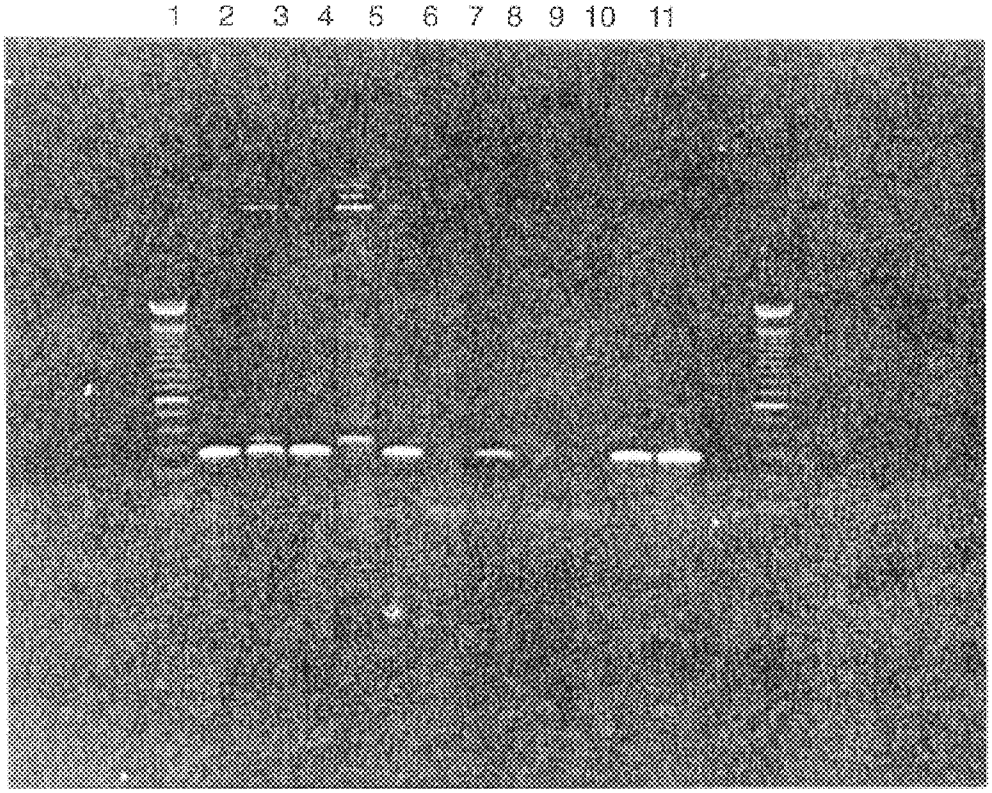
FIG. 2 shows typical results of agarose gel electrophoresis demonstrating the existence of alternatively-spliced fit-coding sequences in various tissue samples.

It was found that certain tissues gave rise to PCR amplification products of notably larger size (as judged by agarose gel electrophoresis) than observed for the full length FLT cDNA product. Typical results are shown in FIG. 2.

PCR products obtained using the nested set of primers A–D were run out on a gel. Lanes 1–3 are products obtained from primary tissue samples of the ovarian carcinomas designated 17, 17R and 25R. Lanes 4 to 7 are products obtained from cell lines established from the ovarian carcinomas 7, 17R, 25 and 25R. Lanes 8 to 10 are the cell lines HEC 1-A, HEC 1-B and Ishikawa respectively. Lane 11 contains products from HUVECs.

The standard size band was of the expected size (around 285 bp) and was found to be identical to the 3' end of the published fit sequence (Shibuya et al., 1990 Oncogene 5, 519–524). However it can be clearly seen that in addition to the full length fit cDNA PCR-amplified product, in lanes 2 (17R, primary tissue) and 4 (7, cell line) are larger bands of approximately 360 bp. A faint band of similar size was also apparent in lane 5 (17R, cell line) but is not clearly seen when the gel photograph is reproduced. These larger bands were extracted from the gel by known techniques and subcloned into the plasmid vector pBluescript II KS and then subjected to sequence analysis using the dideoxynucleotide sequencing method (Sanger et al., 1977 PNAS 71, 5463–5467).

Figure 3:
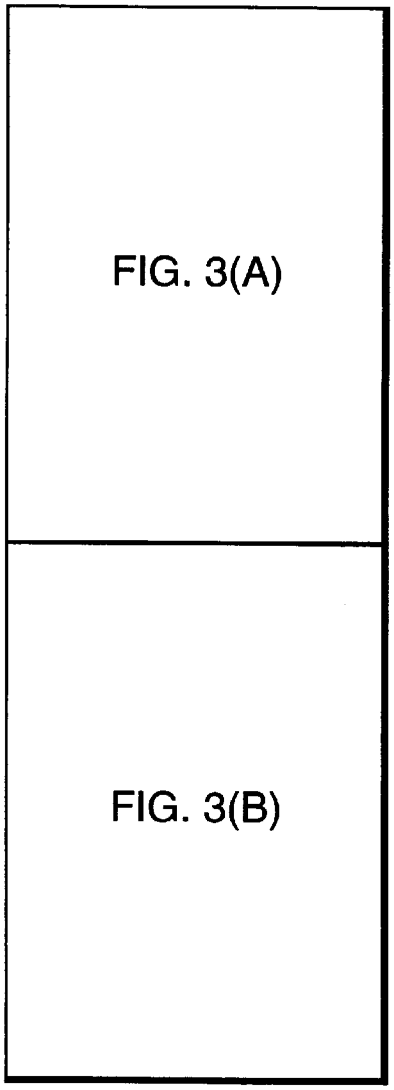
FIG. 3 shows the nucleotide sequence of the 3' region of the sequences encoding full length VEGF receptors (FLT (SEQ ID NO:5) and the related receptor KDR (SEQ ID NO:4)), together with two sequences, FLT4 (SEQ ID NO:6) and FLT15 (SEQ ID NO:7), which encode polypeptides according to the invention.

Sequencing of five independent clones (Boocock et al., 1995 J. Natl. Cancer Inst. 87, 506–516) revealed that each contained one of two novel insertions within the published fit sequence, in the region between the primers. Three of these clones (termed FLT5, FLT15 and FLT16) contained an 85 bp insertion at about position 1555, whilst two other clones (FLT13 & FLT14) contained a 65 bp insertion at about position 1665 (see FIG. 3, numbering based on that of Shibuya et al., 1990 cited above). The insertions account for the larger band size of the PCR products. However, both insertions contain an in-frame termination codon, so that corresponding full length RNAs would encode soluble, truncated receptor variants comprising the first five immunoglobulin-like domains of the extracellular region, up to amino acid 517 or 553, with either 24 or 14 (of which 13 are additional) unrelated amino acids at the C-terminus.

Although these variant fit clones were derived from partial cDNAs encoding only amino acids 503 onward, PCR products of the sizes predicted for corresponding full length cDNAs were amplified from cDNA derived from HUVEC cells, human chorion and ovarian carcinoma cell line 7, using primers specific for each of the novel insertions together with a primer binding just 5' of the initiating ATG (data not shown).

Figures 4A, 4B, 4C, 4D:
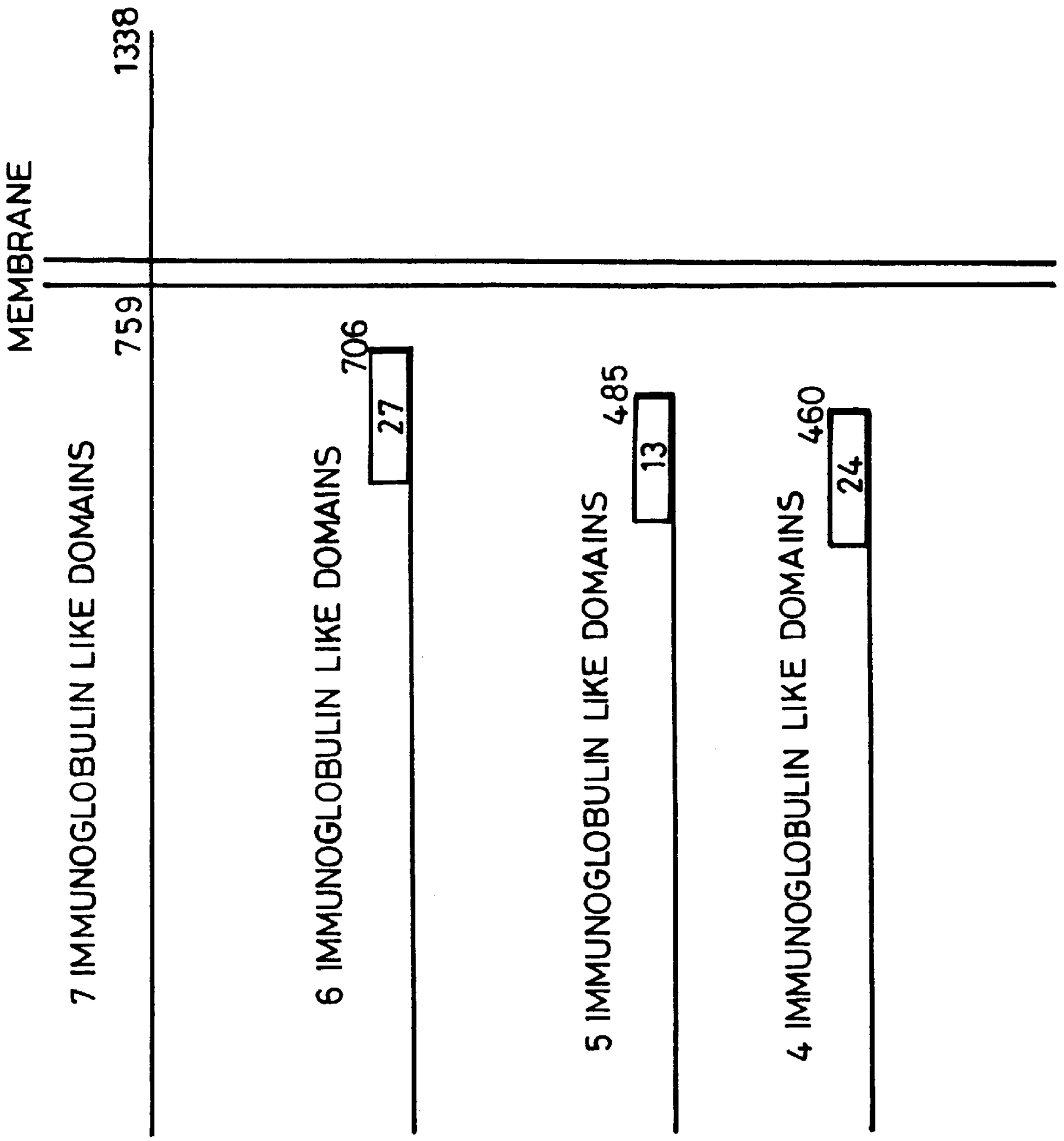
FIG. 4 is a schematic representation of wild type and mutant FLT molecules.

FIG. 4 is a schematic representation of various FLT receptor molecules. At the top, (a) shows the wild type, full length FLT receptor molecule, (b) represents the truncated version described by Kendall & Thomas, (c) represents the polypeptide encoded by FLT4 and (d) represents the polypeptide encoded by FLT15. The numerals at the right show the number of amino acids in the molecule and numerals in the boxes represent the number of amino acids present in the sFLT variants but not in the wild type molecule.

FIG. 5 shows the predicted C terminal amino acid sequence of the polypeptides which would be encoded by "full length" FLT4 and FLT15 clones (i.e. clones which contained all the nucleotide sequence 5' of the primer site used to generate the actual clones). The last 14 amino acids (SEQ ID NO:16) of the FLT4 clone, and the last 24 amino acids (SEQ ID NO:17) of the FLT15 clone, are divergent from the wild type FLT sequence.

We claim:

1. An isolated, soluble polypeptide selected from the group consisting of:
   (a) a polypeptide having an amino acid sequence consisting of amino acid residues 1 to 553 of SEQ ID NO:3;
   (b) a polypeptide having an amino acid sequence consisting of amino acid residues 1 to 517 of SEQ ID NO:3;
   (c) a polypeptide having an amino acid sequence consisting of amino acid residues 1 to 553 of SEQ ID NO:3 with the addition of the sequence ELSNFECLHPCSQE (SEQ ID NO:16) at its C-terminal end;
   (d) a polypeptide having an amino acid sequence consisting of amino acid residues 1 to 517 of SEQ ID NO:3 with the addition of the sequence LPPADSSFMLPPTSFSSNYFHFLP (SEQ ID NO:17) at its C-terminal end; and
   (e) a truncated variant polypeptide of (a), (b), (c) or (d); wherein said truncated variant polypeptide consists of no more than five complete immunoglobulin-like domains; and wherin said trucated variant polypeptide both binds to and exerts an inhibitory effect on VEGF.

2. The isolated soluble polypeptide of claim 1 which is a truncated variant polypeptide that consists of no more than four complete immunoglobulin-like domains.

3. The isolated soluble polypeptide of claim 1 which is a truncated variant polypeptide that consists of from about 400 to about 500 amino acid residues.

4. An isolated nucleic acid having a nucleotide sequence that encodes the isolated soluble polypeptide of claim 1 part (a),(b),(c) or (d), or claim 3.

5. A method for inhibiting VEGF in vitro comprising adding an effective amount of the isolated soluble polypeptide of claims 1, 2 or 3.

6. A pharmaceutical composition comprising the isolated soluble polypeptide of claims 1, 2 or 3, and a physiologically acceptable carrier.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
(A) LENGTH: 976 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:1:

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415
```

-continued

```
Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830
```

-continued

```
Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
    850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975
```

(2) INFORMATION FOR SEQ ID NO:2:

(i) SEQUENCE CHARACTERISTICS:
(A) LENGTH: 972 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:2:

```
Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205
```

-continued

```
Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Val Ala Cys Met Ser Ile Met Ala Leu
        515                 520                 525

Leu Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620
```

-continued

```
Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

(2) INFORMATION FOR SEQ ID NO:3:

(i) SEQUENCE CHARACTERISTICS:
(A) LENGTH: 1338 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:3:

-continued

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415
```

-continued

```
Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Leu Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845
```

-continued

```
Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
        1075                1080                1085

Leu Trp Glu Ile Phe Ser Leu Gly Gly Ser Pro Tyr Pro Gly Val Gln
    1090                1095                1100

Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
                1125                1130                1135

Trp His Arg Asp Pro Lys Glu Arg Pro Arg Phe Ala Glu Leu Val Glu
            1140                1145                1150

Lys Leu Gly Asp Leu Leu Gln Ala Asn Val Gln Gln Asp Gly Lys Asp
        1155                1160                1165

Tyr Ile Pro Ile Asn Ala Ile Leu Thr Gly Asn Ser Gly Phe Thr Tyr
    1170                1175                1180

Ser Thr Pro Ala Phe Ser Glu Asp Phe Phe Lys Glu Ser Ile Ser Ala
1185                1190                1195                1200

Pro Lys Phe Asn Ser Gly Ser Ser Asp Asp Val Arg Tyr Val Asn Ala
                1205                1210                1215

Phe Lys Phe Met Ser Leu Glu Arg Ile Lys Thr Phe Glu Glu Leu Leu
            1220                1225                1230

Pro Asn Ala Thr Ser Met Phe Asp Asp Tyr Gln Gly Asp Ser Ser Thr
        1235                1240                1245

Leu Leu Ala Ser Pro Met Leu Lys Arg Phe Thr Trp Thr Asp Ser Lys
    1250                1255                1260
```

-continued

```
Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
                1285                1290                1295

Cys Gly His Val Ser Glu Gly Lys Arg Arg Phe Thr Tyr Asp His Ala
            1300                1305                1310

Glu Leu Glu Arg Lys Ile Ala Cys Cys Ser Pro Pro Pro Asp Tyr Asn
        1315                1320                1325

Ser Val Val Leu Tyr Ser Thr Pro Pro Ile
    1330                1335
```

(2) INFORMATION FOR SEQ ID NO:4:

(i) SEQUENCE CHARACTERISTICS:
(A) LENGTH: 398 base pairs
(B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO:4:

```
AGAGTGCGCC AACGAGCCCA GCCAAGCTGT CTCAGTGACA AACCCATACC CTTGTGAAGA     60

ATGGAGAAGT GTGGAGGACT TCCAGGGAGG AAATAAAATT GAAGTTAATA AAAATCAATT    120

TGCTCTAATT GAAGGAAAAA ACAAAACTGT AAGTACCCTT GTTATCCAAG CGGCAAATGT    180

GTCAGCTTTG TACAAATGTG AAGCGGTCAA CAAAGTCGGG AGAGGAGAGA GGGTGATCTC    240

CTTCCACGTG ACCAGGGGTC CTGAAATTAC TTTGCAACCT GACATGCAGC CCACTGAGCA    300

GGAGAGCGTG TCTTTGTGGT GCACTGCAGA CAGATCTACG TTTGAGAACC TCACATGGTA    360

CAAGCTTGGC CCACAGCCTC TGCCAATCCA TGTGGGAG                            398
```

(2) INFORMATION FOR SEQ ID NO:5:

(i) SEQUENCE CHARACTERISTICS:
(A) LENGTH: 551 base pairs
(B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO:5:

```
ACCCCTGTAA CCATAATCAT TCCGAAGCAA GGTGTGACTT TTGTTCCAAT AATGAAGAGT     60

CCTTTATCCT GGATGCTGAC AGCAACATGG GAAACAGAAT TGAGAGCATC ACTCAGCGCA    120

TGGCAATAAT AGAAGGAAAG AATAAGATGG CTAGCACCTT GGTTGTGGCT GACTCTAGAA    180

TTTCTGGAAT CTACATTTGC ATAGCTTCCA ATAAAGTTGG GACTGTGGGA AGAAACATAA    240

GCTTTTATAT CACAGATGTG CCAAATGGGT TTCATGTTAA CTTGGAAAAA ATGCCGACGG    300

AAGGAGAGGA CCTGAAACTG TCTTGCACAG TTAACAAGTT CTTATACAGA GACGTTACTT    360

GGATTTTACT GCGGACAGTT AATAACAGAA CAATGCACTA CAGTATTAGC AAGCAAAAAA    420

TGGCCATCAC TAAGGAGCAC TCCATCACTC TTAATCTTAC CATCATGAAT GTTTCCCTGC    480

AAGATTCAGG CACCTATGCC TGCAGAGCCA GGAATGTATA CACAGGGGAA GAAATCCTCC    540

AGAAGAAAGA A                                                         551
```

-continued (2) INFORMATION FOR SEQ ID NO:6:

(i) SEQUENCE CHARACTERISTICS:
(A) LENGTH: 338 base pairs
(B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO:6:

GAGAGCATCA CTCAGCGCAT GGCAATAATA GAAGGAAAGA ATAAGATGGC TAGCACCTTG 60

GTTGTGGCTG ACTCTAGAAT TTCTGGAATC TACATTTGCA TAGCTTCCAA TAAAGTTGGG 120

ACTGTGGGAA GAAACATAAG CTTTTATATC ACAGAATTGT CAAACTTTGA GTGCCTTCAT 180

CCTTGCTCTC AGGAATAGAA CTCTACCTCA TCGGATCTCA TGTGCCAAAT GGGTTTCATG 240

TTAACTTGGA AAAAATGCCG ACGGAAGGAG AGGACCTGAA ACTGTCTTGC ACAGTTAACA 300

AGTTCTTATA CAGAGACGTT ACTTGGATTT TACTGCGG 338

(2) INFORMATION FOR SEQ ID NO:7:

(i) SEQUENCE CHARACTERISTICS:
(A) LENGTH: 358 base pairs
(B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO:7:

GAGAGCATCA CTCAGCGCAT GGCAATAATA GAAGGAAAGA ATAAGCTTCC ACCAGCTGAC 60

AGTTCTTTCA TGTTGCCACC TACAAGCTTC TCTTCCAACT ACTTCCATTT CCTTCCGTGA 120

CTCTAAACGG ATGGCTAGCA CCTTGGTTGT GGCTGACTCT AGAATTTCTG GAATCTACAT 180

TTGCATAGCT TCCAATAAAG TTGGGACTGT GGGAAGAAAC ATAAGCTTTT ATATCACAGA 240

TGTGCCAAAT GGGTTTCATG TTAACTTGGA AAAAATGCCG ACGGAAGGAG AGGACCTGAA 300

ACTGTCTTGC ACAGTTAACA AGTTCTTATA CAGAGACGTT ACTTGGATTT TACTGCGG 358

(2) INFORMATION FOR SEQ ID NO:8:

(i) SEQUENCE CHARACTERISTICS:
(A) LENGTH: 65 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:8:

Glu Ser Ile Thr Gln Arg Met Ala Ile Ile Glu Gly Lys Asn Lys Met
1 5 10 15

Ala Ser Thr Leu Val Val Ala Asp Ser Arg Ile Ser Gly Ile Tyr Ile
20 25 30

Cys Ile Ala Ser Asn Lys Val Gly Thr Val Gly Arg Asn Ile Ser Phe
35 40 45

Tyr Ile Thr Glu Leu Ser Asn Phe Glu Cys Leu His Pro Cys Ser Gln
50 55 60

-continued

Glu
65

(2) INFORMATION FOR SEQ ID NO:9:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:9:

```
Glu Ser Ile Thr Gln Arg Met Ala Ile Ile Glu Gly Lys Asn Lys Leu
1               5                   10                  15

Pro Pro Ala Asp Ser Ser Phe Met Leu Pro Pro Thr Ser Phe Ser Ser
            20                  25                  30

Asn Tyr Phe His Phe Leu Pro
        35
```

(2) INFORMATION FOR SEQ ID NO:10:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:10:

GCAAGGTGTG ACTTTGTTC 19

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:11:

AGGATTTCTT CCCCTGTGTA 20

(2) INFORMATION FOR SEQ ID NO:12:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:12:

GCAAGGTGTG ACTTTTGTTC 20

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:13:

GCGCTCGAGA GCATCACTCA G 21

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:14:

GCGCGGCCGC AGTAAAATCC A 21

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "PRIMER"

(iii) HYPOTHETICAL: NO (xi) SEQUENCE DESCRIPTION: SEQ ID NO:15:

AGGATTTCTT CCCCTGTGTA 20

(2) INFORMATION FOR SEQ ID NO:16:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:16:

Glu Leu Ser Asn Phe Glu Cys Leu His Pro Cys Ser Gln Glu
1 5 10

(2) INFORMATION FOR SEQ ID NO:17:

(i) SEQUENCE CHARACTERISTICS:
(A) LENGTH: 24 amino acids
(B) TYPE: amino acid

```
        (C) STRANDEDNESS: single
        (D) TOPOLOGY: linear

    (ii) MOLECULE TYPE: protein

    (iii) HYPOTHETICAL: NO

    (xi) SEQUENCE DESCRIPTION: SEQ ID NO:17:

Leu Pro Pro Ala Asp Ser Ser Phe Met Leu Pro Pro Thr Ser Phe Ser
1               5                   10                  15

Ser Asn Tyr Phe His Phe Leu Pro
            20
```